United States Patent [19]

Gebauer et al.

[11] Patent Number: 4,631,146

[45] Date of Patent: Dec. 23, 1986

[54] ALPHA-TERTIARY DIMETHYLACETALS AND THEIR USE AS FRAGRANT SUBSTANCES

[75] Inventors: Helmut Gebauer; Marlies Regiert, both of Munich, Fed. Rep. of Germany

[73] Assignee: Consortium fur elektrochemische Industrie GmbH, Munich, Fed. Rep. of Germany

[21] Appl. No.: 831,156

[22] Filed: Feb. 19, 1986

Related U.S. Application Data

[63] Continuation of Ser. No. 639,498, Aug. 10, 1984, abandoned.

[30] Foreign Application Priority Data

Nov. 17, 1983 [DE] Fed. Rep. of Germany ....... 3341605

[51] Int. Cl.$^4$ .................. C07C 43/303; C11D 3/50; C11D 9/44; C11B 9/00
[52] U.S. Cl. .................. 252/522 R; 568/592; 568/596; 252/174.11
[58] Field of Search ................ 568/592, 596; 252/522 R, 174.11

[56] References Cited

U.S. PATENT DOCUMENTS

| | | | |
|---|---|---|---|
| 2,976,327 | 3/1961 | Dorsky et al. | 568/592 |
| 3,428,694 | 2/1969 | Marbet | 568/592 X |
| 4,136,124 | 1/1979 | Zink-Allmong et al. | 568/592 X |

FOREIGN PATENT DOCUMENTS

58-55440  4/1983  Japan ................................. 568/592

*Primary Examiner*—Bernard Helfin
*Attorney, Agent, or Firm*—Collard, Roe & Galgano

[57] ABSTRACT

The invention relates to 1,1-dimethoxy-2,5-dimethyl-2-vinyl-4-hexene, 1,1-dimethoxy-2,2,5-trimethyl-4-hexene, and 1,1-dimethoxy-2,2-dimethyl-3-phenyl-propane. The invention also relates to the production of these compounds and their use as fragrant substances in the cosmetics, detergent and perfume industries.

7 Claims, No Drawings

ALPHA-TERTIARY DIMETHYLACETALS AND THEIR USE AS FRAGRANT SUBSTANCES

This application is a continuation of application Ser. No. 639,498, filed 8/10/84 and now abandoned.

The present invention relates to a select group of α-tertiary dimethylacetals, their production and use as fragrant substances.

2,5-dimethyl-2-vinyl-4-hexenal is known from CA 53 (1959) 10274 f. The compound has a flavor reminiscent of lemon. Moreover, from CA 53 10274 g the corresponding diethylacetal is known which has a slight odor of green leaves.

Furthermore, vapor pressure measurements have been published, which, among others, were made with the fragrant substance 2,2,5-trimethyl-4-hexenal. In connection with this, reference is made to CA 82 (1975) 64321 f.

Moreover, according to DE-OS No. 31 39 358, 2.2-dimethyl-3-phenyl-propanol is known as a fragrant substance.

The aldehydes mentioned above are not alkali-stable and are therefore not useful to impart fragrance to soaps or detergents and many other products.

It is therefore the object of the invention to provide fragrant substances which are alkali-stable, which can be used for imparting fragrance to, among others, soaps, cosmetics and detergents, and which may form a component of colognes having, in addition to alkali-stability, the required nuance for these products.

A narrow selection of α-tertiary dimethyl acetals have been found which are fragrant substances fulfilling the required purpose.

The invention relates to the following group of compounds:

1,1-dimethoxy-2,5-dimethyl-2-vinyl-4-hexene,
1,1-dimethoxy-2,2,5-trimethyl-4-hexene, and
1,1-dimethoxy-2,2-dimethyl-3-phenyl-propane.

The compounds according to the invention are illustrated by the general formula

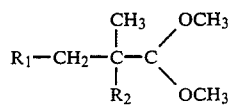

wherein $R_1$ is the 2,2-dimethyl vinyl group when $R_2$ represents methyl or vinyl, and wherein $R_1$ represents phenyl when $R_2$ is methyl.

The compounds according to the invention are obtained by acetalization of the corresponding aldehydes with methanol. A preferred method for preparing the compounds according to the invention is characterized by reacting 2,5-dimethyl-2-vinyl-4-hexenal, 2,2,5-trimethyl-4-hexenal or 2,2-dimethyl-3-phenyl-propanal with methanol in the presence of anhydrous calcium salts.

Methanol is used in at least equimolar amounts, i.e., at least 2 moles per 1 mole of acetal to be reacted. However, in most cases methanol also acts as solvent and is used in higher excess. Examples of suitable anhydrous calcium salts are calcium chloride, calcium carbonate, calcium oxide, calcium hydroxide and calcium phosphate, but calcium chloride and calcium oxide are preferred. The amount of the calcium salt to be used is so adjusted that it is capable of absorbing at least the amount of water which is released by the reaction. It amounts to 0.1-1 mole and, preferably, 0.2-0.4 moles per mole of reacting aldehyde.

In order to accelerate the reaction, frequently catalytically effective amounts of ammonium nitrate are added to the reaction mixture. Preferably, the amount is 0.01 to 0.1 moles per mole of the aldehyde.

The aldehydes used as starting materials are obtainable in a one-pot process from base chemicals:

2,5-dimethyl-2-vinyl-4-hexenal is obtained by reaction of tiglic aldehyde with prenyl chloride;

2,2,5-trimethyl-4-hexenal is obtained by reaction of isobutyric aldehyde with prenyl chloride; and 2,2-dimethyl-3-phenyl-propanal is obtained by reaction of isobutyric aldehyde with benzyl chloride in an organic/alkaline 2-phase system in the presence of a phase transfer-catalyst.

Per 1 mole of isobutyric aldehyde or tiglic aldehyde, about 1–1.2 moles of prenyl chloride or benzyl chloride, respectively, are used.

The organic/alkaline 2-phase system is formed from an organic inert solvent, immiscible with water and an alkali metal hydroxide present in a 5–50% aqueous solution or in a solid state.

As phase transfer catalysts, e.g., crown ether, quaternary ammonium and phosphonium salts are used in amounts of 0.5–5 mole % relative to prenyl chloride or benzyl chloride, respectively.

The reaction temperatures are 20°–150° C., and, preferably, 60°–70° C. Advantageously, the process is carried out by first introducing the 2-phase system with the catalyst, and a mixture of the reaction components is then added drop by drop.

The precedingly described procedure of synthesis is a preferred method for the production of the dimethylacetals according to the invention, which is characterized by:

(a) reacting isobutyric aldehyde or tiglic aldehyde, respectively, in a one-pot process with prenyl chloride or benzyl chloride, respectively, in an organic/alkaline 2-phase system in the presencce of a phase transfer catalyst; and (b) reacting the aldehyde with methanol in the presence of anhydrous calcium salts.

1,1-Dimethoxy-2,5-dimethyl-2-vinyl-4-hexene is a fragrant substance of sweet, fruity, slightly bitter aroma which exhibits a strong lemon fragrance. Defining the substance is the naturally acting aroma characteristic of basic notes of bergamot oil, petit grain oil, orange oil having bitter as well as flower-like accents. The fragrant substance according to the invention blends with aroma complexes such as neroli oil, bergamot, lavender, and lemon. Its preferred field of use is in the production of soaps, alkali-stable colognes and other fruity-flowery compositions.

1,1-Dimethoxy-2,2,5-trimethyl-4-hexene is a fragrant substance of fresh-fruity aroma reminiscent of grapefruit. The fragrant substance according to the invention imparts to compositions such as Fougére, Chypre, Eau de Cologne fresh, vivid top notes.

1,1-Dimethoxy-2,2-dimethyl-3-phenyl-propane is a fragrant substance of sweet-fruity aroma with flowery nuances. The dominant odor is, however, a slightly bitter citrus component which is reminiscent of grapefruit rind and bergamot oil. The substance according to the invention imparts to fruity and flowery compositions, freshness and sweetness. Due to its good adherence, it is particularly valuable as hearty and base notes.

The fragrant substances according to the invention are used for aromatization of cosmetic and technical products, either alone or especially in combination with other fragrant substances. The substances according to the invention are alkali-stable. They therefore open up fields of application in the sector of detergents, soaps, hair conditioners, and colognes stable to soaps.

In the following, the invention will be more fully described in a number of examples, but it should be understood that these are given by way of illustration and not of limitation. The amounts mentioned in the following with respect to the composition of mixtures of fragrant substances are parts by weight.

EXAMPLE 1

Preparation of 1,1-dimethoxy-2,2-dimethyl-3-phenyl-propane

Into a flask containing 162 g (1 mole) of 1,1-dimethoxy-2,2-dimethyl-3-phenyl-propanal, 5 g of ammonium nitrate, and 300 ml of methanol, and 37 g of anhydrous calcium chloride were added in portions, while stirring. Then 1 ml of 85% phosphoric acid was added. The reaction temperature was 40° C. The reaction was terminated after 6 hours. Finally, the reaction mixture was neutralized with 2 n sodium hydroxide and the inorganic phase was separated. For processing the organic phase, methanol was first withdrawn and then distillation took place over a Vigreux column. The desired end product was obtained as colorless liquid at 120° C. and a pressure of 16 mbar. The yield was 156 g corresponding to 75% of the theoretical. Index of refraction at 20° C. 1:494.

EXAMPLE 2

Preparation of 1,1-dimethoxy-2,5-dimethyl-2-vinyl-4-hexene

The procedure of Example 1 was repeated, with the modification that, instead of 1 mole of 2,2-dimethyl-3-phenyl-propanal, 1 mole of 2,5-dimethyl-2-vinyl-4-hexenal was used. The desired end product was obtained as a colorless liquid at 94° C. and 16 mbar. The yield was 178.5 g corresponding to 90% of the theoretical. Index of refraction at 20° C. 1:456.

EXAMPLE 3

Preparation of 1,1-dimethoxy-2,2,5-trimethyl-4-hexene

The procedure of Example 1 was repeated with the modification that, instead of 2,2-dimethyl-3-phenyl-propanal, 1 mole of 2,2,5-trimethyl-4-hexenal was used. The desired end product was obtained as a colorless liquid at 82° C. and 16 mbar. The yield was 149 g corresponding to 80% of the theoretical. Index of refraction at 20° C. 1:441.

EXAMPLE 4

1,1-Dimethoxy-2,2-dimethyl-3-phenyl-propane as a fragrant substance

| Sweet-Flowery Perfume Oil | a | b |
|---|---|---|
| Phenylethyl alcohol | 70 | 70 |
| Hydroxycitronellal | 200 | 200 |
| Verdyl acetate (Givaudan Corp.) | 60 | 60 |
| Sandalwood Oil | 55 | 55 |
| Jasmine Synth | 80 | 80 |
| Ketone Musk | 40 | 40 |
| Citronellol | 60 | 60 |
| Ylang-Ylang Oil | 35 | 35 |
| Methylionone | 50 | 50 |
| Benzyl propionate | 60 | 60 |
| Geraniol | 40 | 40 |
| 1,1-Dimethoxy-2,2-dimethyl-3-phenyl-propane | — | 250 |
| | 750 | 1000 |

The flowery composition according to a gains by addition of 250 parts of 1,1-dimethoxy-2,2-dimethyl-3-phenyl-propane according to b in penetrating strength and naturalness. The ionone note is stressed and the fruity nuances become stronger.

EXAMPLE 5

1,1-Dimethoxy-2,2-dimethyl-3-phenyl-propane as a fragrant substance

| Perfume Oil with Fougere Note | a | b |
|---|---|---|
| Bergamot Oil | 200 | 200 |
| Coumarin | 220 | 220 |
| Lavandin Oil | 100 | 100 |
| Vetiver Oil | 20 | 20 |
| Linalyl acetate | 30 | 30 |
| Terpinyl acetate | 30 | 30 |
| Phenylethyl alcohol | 50 | 50 |
| Geranium Oil | 30 | 30 |
| Oak Moss Extract | 10 | 10 |
| Patschouli Oil | 20 | 20 |
| Galaxolide (I.F.F.) | 20 | 20 |
| Benzyl acetate | 40 | 40 |
| α-Amyl-cinnamicaldehyde | 30 | 30 |
| 1,1-dimethoxy-2,2-dimethyl-3-phenyl-propane | — | 200 |
| | 800 | 1000 |

The aroma complex according to a is a Fougére-type with a dominant coumarin note. By the addition of 200 parts 1,1-dimethoxy-2,2-dimethyl-3-phenyl-propane (according to b) the warm-herbaceous character is repressed, and the composition becomes more penetrating. The powdery sweetness hightens the aromatic effect of the base.

EXAMPLE 6

1,1-Dimethoxy-2,5-dimethyl-2-vinyl-4-hexene as a fragrant substance

| Perfume Oil With Fresh Flowery Note | a | b |
|---|---|---|
| Hydroxycitronellal | 150 | 150 |
| Bergamot Oil | 200 | 200 |
| Jasmine synth | 120 | 120 |
| 6-methyl-α-ionone | 120 | 120 |
| Benzyl acetate | 100 | 100 |
| Heliotropin | 70 | 70 |
| Dimethylbenzyl carbinol | 30 | 30 |
| Fennel Oil (sweet) | 20 | 20 |
| Oak Moss Extract | 20 | 20 |
| Benzyl benzoate | 60 | 60 |
| 1,1-dimethoxy-2,5-dimethyl-2-vinyl-4-hexene | — | 110 |
| | 890 | 1000 |

The perfume oil according to a can be described as sweet-flowery and is reminiscent of the aroma of Lily in the Valley. By addition of 110 parts of 1,1-dimethoxy-2,5-dimethyl-2-vinyl-4-hexene according to b the sweet-flowery aroma obtains a highlight of a vivid, fresh and natural note.

EXAMPLE 7

1,1-Dimethoxy-2,5-dimethyl-2-vinyl-4-hexene as a fragrant substance

| Perfume Oil With Lemony-Fresh Note | a | b |
|---|---|---|
| Litsea Cubeba oil chin | 170 | 170 |
| Grapefruit Oil | 180 | 180 |
| Citronellol | 160 | 160 |
| Bergamot Oil | 60 | 60 |
| Lemon Oil | 100 | 100 |
| Sandalwood Oil | 20 | 20 |
| Ethylvanillin | 16 | 16 |
| Coumarin | 10 | 10 |
| Heliotropin | 20 | 20 |
| Methylanthranilate | 34 | 34 |
| iso-Eugenol | 40 | 40 |
| Geraniol | 90 | 90 |
| 1,1-dimethoxy-2,5-dimethyl-2-vinyl-4-hexene | — | 100 |
|  | 900 | 1000 |

The perfume oil according to a is of a sour oriental-fruit type mixed with flowery accents. By the addition of 100 parts of 1,1-dimethoxy-2,5-dimethyl-2-vinyl-4-hexene, an aroma complex b is obtained having a fresh-tart odor in addition to the flowery accents; the fruity note is reinforced.

EXAMPLE 8

1,1-Dimethoxy-2,2,5-trimethyl-4-hexene as a fragrant substance

| Perfume Oil With Fougere-Note | a | b |
|---|---|---|
| Bergamot Oil | 230 | 230 |
| Coumarin | 230 | 230 |
| Spike Oil, Spanish | 110 | 110 |
| Terpinyl acetate | 30 | 30 |
| Linalyl acetate | 30 | 30 |
| Tree Moss abs. 5% in DPG | 60 | 60 |
| Patschouli Oil | 20 | 20 |
| Ketone Musk | 40 | 40 |
| Phenylethyl alcohol | 60 | 60 |
| Vetiver Oil, Java | 30 | 30 |
| Benzyl acetate | 40 | 40 |
| α-Amyl-cinnamic aldehyde | 30 | 30 |
| 1,1-dimethoxy-2,2,5-trimethyl-4-hexene | — | 90 |
|  | 910 | 1000 |

The perfume oil has a sweet, spicy basic aroma with woody side notes. By the addition of 90 parts 1,1-dimethoxy-2,2,5-trimethyl-4-hexene a base b is obtained which compared to a is stronger and fresher. It is useful in men's cologne.

EXAMPLE 9

1,1-Dimethoxy-2,2,5-trimethyl-4-hexene as a fragrant substance

| Perfume Oil In The Direction Of "Chypre" | a | b |
|---|---|---|
| Hydroxycitronellal | 110 | 110 |
| Bergamot Oil | 130 | 130 |
| Jasmine Oil | 90 | 90 |
| Phenylethyl alcohol | 90 | 90 |
| α-Hexyl-cinnamic aldehyde | 70 | 70 |
| Methylionone | 50 | 50 |
| Ambrette Musk | 60 | 60 |

| -continued Perfume Oil In The Direction Of "Chypre" | a | b |
|---|---|---|
| Oak Moss Extract | 40 | 40 |
| Styrallyl acetate | 15 | 15 |
| gamma-Decalactone | 10 | 10 |
| Civet 5% in DPG | 40 | 40 |
| Linalool | 55 | 55 |
| Sandalwood Oil | 40 | 40 |
| Orange Oil, bitter | 40 | 40 |
| Ethylvanillin | 30 | 30 |
| Benzyl acetate | 40 | 40 |
| 1,1-dimethoxy-2,2,5-trimethyl-4-hexene | — | 90 |
|  | 910 | 1000 |

The feminine aroma complex according to a may be characterized as sweet and slightly flowery. By the addition of 90 parts of 1,1-dimethoxy-2,2,5-trimethyl-4-hexene the aroma complex is vividly highlighted. The characteristic is now flowery and fresh.

EXAMPLE 10

Stability Test 1,1-dimethoxy-2,5-dimethyl-2-vinyl-4-hexene, 1,1-dimethoxy-2,2,5-trimethyl-4-hexene, and 1,1-dimethoxy-2,2-dimethyl-3-phenyl-propane were stored with neutral or alkaline media 60 days at 40° C. Then they were tested for change in color and odor, and compared with freshly prepared solutions. The solutions were also tested by means of thin-sheet chromatography.

Each of these tests was repeated four times; 0.5% solutions of the fragrant substances according to the invention were prepared in 60% aqueous ethanol. The alkaline solutions were adjusted to pH 14 by addition of 0.1 n NaOH.

Test solution 1 pH=7
Test solution 2 pH=14

Under the conditions described above, the three fragrant substances according to the invention were stable in all test solutions. No changes of color or odor could be found. The thin-sheet chromatograms did not show any hint of chemical changes.

While only several examples of the present invention have been described, it is obvious that many changes and modifications may be made thereunto, without departing from the spirit and scope of the invention.

What is claimed is:

1. An α-tertiary dimethylacetal selected from the group consisting of 1,1-dimethoxy-2,5-dimethyl-2-vinyl-4-hexene, 1,1-dimethoxy-2,2,5-trimethyl-4-hexene and 1,1-dimethoxy-2,2-dimethyl-3-phenyl-propane.

2. A cosmetic preparation comprising an effective amount of a compound according to claim 1, as the sole fragrance-imparting substance.

3. A detergent preparation comprising an effective amount of a compound according to claim 1, as the sole fragrance-imparting substance.

4. A perfumery preparation comprising an effective amount of a compound according to claim 1, as the sole fragrance-imparting substance.

5. A cosmetic preparation comprising an effective amount of a compound according to claim 1 as a fragrance-imparting substance, in combination with other fragrance-imparting substances.

6. A detergent preparation comprising an effective amount of a compound according to claim 1 as a fragrance-imparting substance, in combination with other fragrance-imparting substances.

7. A perfumery preparation comprising an effective amount of a compound according to claim 1 as a fragrance-imparting substance, in combination with other fragrance-imparting substances.

* * * * *